(12) United States Patent
Kleijnen et al.

(10) Patent No.: US 11,877,837 B2
(45) Date of Patent: Jan. 23, 2024

(54) APPARATUS FOR USE IN INDUCTIVE SENSING

(71) Applicant: KONINKLIJKE PHILIPS N.V., Eindhoven (NL)

(72) Inventors: Mark Peter Paul Kleijnen, Eindhoven (NL); Rick Bezemer, Eindhoven (NL); Wouter Herman Peeters, Eindhoven (NL); Gerardus Johannes Nicolaas Doodeman, Eindhoven (NL); Tim Patrick Steunebrink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 194 days.

(21) Appl. No.: 17/440,236

(22) PCT Filed: Mar. 17, 2020

(86) PCT No.: PCT/EP2020/057182
§ 371 (c)(1),
(2) Date: Sep. 17, 2021

(87) PCT Pub. No.: WO2020/187869
PCT Pub. Date: Sep. 24, 2020

(65) Prior Publication Data
US 2022/0183581 A1 Jun. 16, 2022

(30) Foreign Application Priority Data
Mar. 18, 2019 (EP) .................................... 19163368

(51) Int. Cl.
*G01R 27/28* (2006.01)
*A61B 5/05* (2021.01)
*G01R 27/26* (2006.01)
*H01Q 7/00* (2006.01)

(52) U.S. Cl.
CPC ............ *A61B 5/05* (2013.01); *G01R 27/2611* (2013.01); *H01Q 7/005* (2013.01)

(58) Field of Classification Search
CPC ............ G01R 27/2611; G01R 29/0878; H01Q 7/005; A61B 5/05; A61B 5/113; H03K 17/954
See application file for complete search history.

(56) References Cited

U.S. PATENT DOCUMENTS

| | | | |
|---|---|---|---|
| 8,441,154 B2 | 5/2013 | Campanella |
| 8,665,086 B2 | 3/2014 | Brogdon |
| 8,669,770 B2 | 3/2014 | Cros |
| 8,772,973 B2 | 7/2014 | Kurs |

(Continued)

OTHER PUBLICATIONS

International Search Report for PCT/EP2020/057182 filed Mar. 17, 2020.

*Primary Examiner* — Thang X Le

(57) ABSTRACT

An apparatus (20) for use in inductive sensing includes a loop antenna (26) and a signal generator (24) for driving the antenna, these forming a resonator circuit (22). The resonator circuit is drivable in a drive state in which the antenna is driven at resonance to thereby generate electromagnetic signals. The arrangement further includes a switching means (28) for switchably inhibiting the drive state of the antenna This allows in use controllable switching of the antenna in and out of the drive state to thereby control switching signal generation on and off.

16 Claims, 5 Drawing Sheets

(56) References Cited

U.S. PATENT DOCUMENTS

| | | |
|---|---|---|
| 8,901,779 B2 | 12/2014 | Campanella |
| 9,106,203 B2 | 8/2015 | Campanella |
| 9,369,182 B2 | 6/2016 | Campanella |
| 9,584,189 B2 | 2/2017 | Campanella |
| 2004/0182852 A1 | 9/2004 | Knappe |
| 2009/0134712 A1* | 5/2009 | Cook ...................... H02J 50/50 307/104 |
| 2012/0105248 A1* | 5/2012 | Miller ..................... H04B 5/02 340/870.01 |
| 2014/0002085 A1* | 1/2014 | Biber .................. G01R 33/365 324/322 |
| 2018/0081006 A1* | 3/2018 | Robb ................. G01R 33/3657 |
| 2018/0123843 A1* | 5/2018 | Teichmann ........ G06K 19/0707 |
| 2019/0336014 A1 | 11/2019 | Bezemer |
| 2019/0343417 A1 | 11/2019 | Bezemer |
| 2020/0178824 A1 | 6/2020 | Bezemer |

\* cited by examiner

APPARATUS FOR USE IN INDUCTIVE SENSING

CROSS-REFERENCE TO PRIOR APPLICATIONS

This application claims the priority benefit under 35 U.S.C. § 371 of International Patent Application No. PCT/EP2020/057182, filed on Mar. 17, 2020, which claims the priority benefit of European Patent Application No. 19163368.4, filed on Mar. 18, 2019, the contents of which are herein incorporated by reference.

FIELD OF THE INVENTION

This invention relates to an induction based sensing arrangement, and in particular including switching means for controlling signal generation.

BACKGROUND OF THE INVENTION

Inductive sensing is based on generation of a primary alternating magnetic field via a primary loop, which leads to the induction of eddy currents and a consequent secondary magnetic field in conductive material or tissue within the primary magnetic field. Interaction of the secondary magnetic field with the primary loop or the primary magnetic field can be used to detect patterns of movement within probed bodies, in particular those comprising a water content.

Of particular advantage is use of inductive sensing for detecting physiological signals, (otherwise known as kymographic signals) such as heartbeats and breathing patterns.

In inductive sensing, a signal generator (such as an oscillator) is connected to a loop antenna. The oscillator is an amplifier, typically consisting of one or more transistors, which induces a resonant state in a coupled circuit, in combination with an inductance source and capacitance source. The inductance is provided by the loop antenna, while the capacitance is provided by an optional capacitor component placed in parallel to the loop, together with parasitic capacitances of the loop with itself and its environment, and the oscillator parasitic capacitances. The total system is called the resonator.

When using a single loop antenna in this way for generation of the primary magnetic field and sensing of the secondary magnetic field, the current through the circuit can often be relatively high. As a result of this, several problems may arise.

First, the current through the loop may often be too high to pass Electromagnetic Compatibility (EMC) or Specific Absorption Rating (SAR) regulations. The current is provided at a certain amplitude to enable clear signal sensing. However, this can cause exceeding of regulatory requirements for limiting power.

Secondly, the system may not be compatible for use within a Magnetic Resonance Imaging (MRI) system, since the RF fields generated by the scanner will likely be disturbed by the inductive sensor. Additionally, the high power of the RF field of the MRI scanner may damage or even destroy the signal generator of the inductive sensing system. Use of inductive sensing within MRI is a key application area for the technology. In particular, the current respiration measurement approach used in known MM devices is a purely mechanical measurement. Inductive sensing offers the potential for improvement. Hence is it restrictive to be prevented from this application area.

Further problems may also arise in systems comprising multiple antenna loops.

First, the magnetic fields of the multiple antennas can interact with one another which can lead to so called 'locking in'. Here, due to strong magnetic coupling, two or more of the inductive sensors lock on to the same frequency, and thus can no longer measure independently.

Secondly, due to the magnetic interaction, the multiple inductive sensors can disturb one other's signals. For example, it may occur that one inductive sensor measures both its own signal, and signals of its neighboring inductive sensors. This can occur even when the sensors are at different frequencies, and have not locked to the same frequency.

There would be advantage in providing an improved sensing arrangement able to overcome one or more of the above problems.

SUMMARY OF THE INVENTION

The invention is defined by the claims.

According to examples in accordance with an aspect of the invention, there is provided an apparatus for use in inductive sensing, comprising a resonator circuit, comprising an antenna, and an electronic signal generator coupled to the antenna, for driving the antenna with a drive signal to cause it to generate electromagnetic signals, the resonator circuit having a resonance frequency, wherein the resonator circuit is configurable in a drive state in which the antenna is driven at resonance to thereby generate electromagnetic signals; and a switching means operable to switchably inhibit said drive state based on interruption, or electrical alteration, of the drive signal or of the resonator circuit, to thereby permit switching of electromagnetic signal generation.

The invention is based on provision of controllable switching means permitting activation or deactivation of signal generation with the antenna. This allows start or stop control of electromagnetic signal generation. A number of different specific switching methods or regimes may be applied in examples to achieve different advantageous effects.

The switching means typically performs some adjustment of the resonator circuit electrical properties which leads to suppression of the drive state. When in operation, the switching means is operable to switch the resonator circuit away from the drive state to a non-drive state.

The switching means may adjust one or more electrical characteristics of the resonator circuit. Electrical characteristics may include for instance a capacitance of the resonance circuit, or a portion of it, an inductance of the resonator circuit or a portion of it, a resistance of the circuit or a portion of it.

The apparatus is for use in inductive sensing, i.e. for use in a system or arrangement for generating electromagnetic signals for application to a body to be investigated, and for sensing returned electromagnetic signals from the body, returned from the body responsive to the applied electromagnetic signals. Thus, the apparatus may otherwise be referred to in this disclosure as a sensing arrangement, and reference to a sensing arrangement or 'arrangement' may be understood as referring to an apparatus according to one or more embodiments of the invention.

The resonance frequency of the resonator circuit means the natural frequency of electronic oscillation of the resonance circuit. It is a product of natural capacitances and inductances within the circuit, as well as optionally an additional capacitor component included in the circuit. The resonance frequency is the current frequency at which the resonator circuit will be at a state of resonance.

Driving the antenna at resonance means driving the antenna to oscillate or the resonator circuit to oscillate at its resonance frequency. It means for instance driving the antenna with a drive signal matching the resonance frequency.

The switching means may comprise an electrical component included in the resonator circuit. It is preferably located electrically, or signally, downstream from the signal generator. This allows inhibiting of the drive state without adjusting the signal generator controls.

The signal generator generates an oscillatory, or periodic, electrical signal. The signal generator may comprise an electronic oscillator.

The antenna is a (magnetic) inductive loop antenna. Preferably the antenna comprises a single loop (to reduce parasitic capacitances between multiple loops).

Preferably, the apparatus further comprises a controller further configured to control the switching means.

Preferably, the controller is configured to control the switching means according to a pre-defined control schedule or control program.

In this embodiment, the controller controls the switching means with a certain program of timings, or based on certain triggers or references, for instance to functions or states of other components in a broader system. This control program or schedule may be programmed in the controller. It may be adjustable, for instance based on a user input command. It may be stored in a local memory or processor.

The controller may be adapted to receive a signal indicative of an active state of an external device, and to control switching to inhibit the drive state of the resonator circuit responsive to said signal.

In particular, the controller may be adapted in use to receive from an external device a signal indicative of a timing of an active state of the external device, and to control the switching such that the drive state of the resonator circuit is inhibited during occurrence of said active state of the external device.

For instance, the controller may be configured to control switching to coincide with activation of one or more other components of a broader system, or an associated system. For instance, the antenna arrangement may be used within a magnetic resonance system, and switching of the circuit out of drive state may be timed to coincide with activation of one or more electromagnetic signal sources (e.g. the primary RF coils) of the MR system. The strong fields of these coils could damage the signal generator. The switching means in this case may be configured to decouple the signal generator from the resonator circuit.

According to an advantageous set of embodiments, the controller may be adapted to implement periodic switching of the switching means, to thereby impose a duty cycle on the drive signal.

This embodiment creates a drive signal which follows a duty cycle. As a result, a time-average output power of electromagnetic signals generated by the system can be reduced. This thus enables regulations compliance in a simple and adjustable way, by controllably reducing the time-average output power, without reducing instantaneous output power during signal transmission periods.

This approach to moderating power output furthermore does not diminish inductive sensing capability in applications for sensing physiological parameters. In particular, the oscillatory parameters typically measured in the body, such as heart movement, or breathing activity, typically have a frequency much lower (order of Hz) than the oscillation frequency of the resonator circuit (e.g. order of MHz). Hence it is not required to have continuous signal acquisition in order to capture the physiological signals. Hence, the reduced duty cycle imposed according to the above example does not affect acquisition of physiological measurements.

A frequency of the periodic switching or the duty cycle may be adjustable to thereby adjust an electromagnetic output power of the apparatus.

Electromagnetic output power means time-average output power, i.e. over a number of cycles of the duty cycle.

A controller may be included in the apparatus, configured to control a frequency of the duty cycle/the periodic switching to control the electromagnetic output power.

The frequency of the duty cycle or periodic switching may be controllable based on a user input command, for instance receivable at the controller via a user interface operatively coupled to the controller.

The switching means may comprise a controllable switch element connected in series between the signal generator and the antenna, permitting switchable decoupling of the antenna from the signal generator (or switchable decoupling of the signal generator from the (rest of the) resonator circuit).

The switching element is a circuit break element, which can switchably introduce a break in the circuit line between the antenna and the signal generator to thereby realize the decoupling.

The switching means may comprise a switch element connected in electrical parallel with the antenna for switchably short-circuiting the resonator circuit.

When the switch is closed, the drive signal current will flow through the parallel switch, rather than through the antenna, so the antenna will not oscillate to generate the electromagnetic signals.

The switching means may be configured to inhibit said drive state based on altering a resonance frequency of the resonator circuit.

By adjusting the circuit resonance frequency, the resonator circuit is detuned, meaning that the oscillatory drive signal generated by the signal generator (of a frequency which previously brought the circuit to resonance) no longer realizes a state of resonance in the resonator circuit. The switching means introduces a mismatch for instance between the frequency of the drive signal and the resonance frequency of the resonator circuit, inhibiting oscillation of the circuit at resonance. Thus, the circuit is kept out of the drive state defined above.

The adjustment of the resonance frequency may be based on adjusting a capacitance of the resonator circuit. The resonator circuit may include a capacitor component which partially defines the resonance frequency of the resonator circuit in this example.

In one set of examples, the resonator circuit may comprise a capacitor connected in parallel with the antenna, and further comprise a switchable circuit break element in series with the capacitor for switchably decoupling the capacitor from the resonator circuit.

The switching means in this embodiment switchably breaks the circuit along the parallel branch or rail containing the capacitor. This leads to the capacitor being decoupled from the antenna, thereby changing a capacitance of the resonator circuit, leading to an alteration of the resonance frequency. This means that the drive signal no longer causes the resonator circuit to oscillate at resonance, thereby deactivating the drive state.

Additionally or alternatively, in a further set of examples, the resonator circuit may include a variable capacitor, and means for controlling switching of a capacitance of the variable capacitor between at least a first and second value, to thereby provide switchable adjustment of the resonance frequency. This thereby provides switchable detuning of the resonator circuit, and thus switchable inhibiting of the drive state.

The switching means here comprises the adjustable capacitor and/or a means for controlling switching of its capacitance.

The means for controlling the capacitance adjustment may be a control circuit included in the variable capacitor, or a separate controller for instance.

The signal generator may include amplification means, and wherein the switching means is comprised by the signal generator, and is adapted to alter an amplification level of the amplification means.

By reducing the amplification for instance, the amplitude of the drive signal is reduced to a sufficient level that the resonator circuit is no longer driven at resonance, and hence the drive state is deactivated.

The resonator circuit may comprise a plurality of antennas operatively coupled to the signal generator, the signal generator operable to supply a drive signal to each of the antennas, and wherein the switching means permits selective inhibiting of the drive state in a selected one or more of the antennas.

Here multiple antennas are connected to a single signal generator, and the switching means is operable to selectively inhibit the drive state in any one or more of the antennas. It may comprise a plurality of separate switch parts, for instance a separate switch in series or parallel with each antenna. It may include a control means for controlling the selective switching, and for instance for controlling the selective switching with the multiple switch parts.

For instance the switching means may comprise a controllable capacitor, having a controllable capacitance.

The apparatus may comprise a plurality of the above described resonator circuits, each comprising an antenna, and there being provided a separate switching means for each resonator circuit, and the apparatus further including a controller for controlling the plurality of switching means.

This represents a further option for providing multiple controllable antennas. Here a separate signal generator is provided for each antenna in addition to a separate switching means, enabling both independent switching and, optionally, independent control of the drive frequency. It also enables the signal generator to be provided close to each antenna, which is beneficial in particular for higher frequencies of operation, where a long connection track can hamper signal transfer.

According to one or more embodiments, switching may be controlled such that no two of the antennas are in a drive state at any one time, i.e. only one antenna is active at any one time.

According to one or more embodiments, switching may be controlled such that, during use, the drive state is inhibited in at least one of the antennas at all times. In other words, switching is controlled so as to prevent all antennas being active (being in drive state) simultaneously at any given time.

Examples in accordance with a further aspect of the invention provide an inductive sensing system, comprising:

an apparatus in accordance with any example or embodiment outlined above or described below, or in accordance with any claim of this application; and a signal processing unit configured to receive and process electromagnetic signals sensed at the antenna of the apparatus to derive one or more sensing measurements.

Examples in accordance with a further aspect of the invention provide an inductive sensing system, comprising:

an apparatus in accordance with any example or embodiment outlined above or described below, or in accordance with any claim of this application; and a signal processing unit configured to detect at the antenna electromagnetic signals returned from the body responsive to the generated electromagnetic signals based on detecting variations over time of electrical characteristics of the resonator circuit.

Optionally, the signal processing unit may be further configured to receive and process said electromagnetic signals sensed at the antenna of the apparatus to derive one or more sensing measurements.

Preferably the signal detection is performed simultaneously with the signal generation.

Examples in accordance with a further aspect of the invention provide a method of configuring an apparatus, the apparatus comprising a resonator circuit comprising a loop antenna, and an electronic signal generator coupled to the antenna, for driving the antenna with a drive signal to cause it to generate electromagnetic signals, the resonator circuit having a resonance frequency, wherein the resonator circuit is configurable in a drive state in which the antenna is driven at resonance to thereby generate electromagnetic signals, and the method comprising controlling switchable inhibiting of said drive state, the inhibiting based on interruption, or electrical alteration, of the drive signal or the resonator circuit, to thereby control start or stop of electromagnetic signals.

Examples in accordance with a further aspect of the invention provide a method, comprising:

driving a resonator circuit with a drive signal to cause it to generate electromagnetic signals, resonator circuit comprising a loop antenna, and an electronic signal generator coupled to the antenna, and the resonator circuit having a resonance frequency, and wherein the resonator circuit is configurable in a drive state in which the antenna is driven at resonance to thereby generate electromagnetic signals, and controlling switchable inhibiting of said drive state, the inhibiting based on interruption, or adjustment of electrical characteristics of, the drive signal or of the resonator circuit, to thereby control start or stop of electromagnetic signals.

According to one or more embodiments, the method may be a medical sensing method. It may comprise positioning at least the loop antenna of the resonator circuit in proximity with a body of a subject, and driving the resonator circuit with said drive signal so as to generate electromagnetic signals for penetrating the body surface.

Preferably the method may further comprise detecting returned electromagnetic signals from the body at the resonator circuit.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
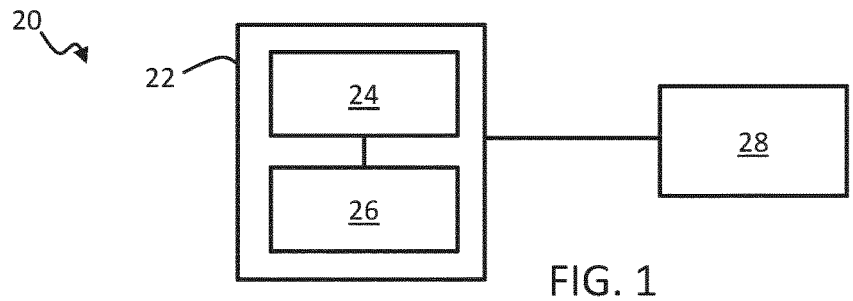
FIG. 1 shows a block diagram of an example sensing arrangement according to one or more embodiments.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an apparatus for use in inductive sensing, the apparatus including an inductive (magnetic) loop antenna (herein: 'antenna'), and a signal generator for driving the antenna, these forming a resonator circuit. The resonator circuit is drivable in a drive state in which the antenna is driven at resonance to thereby generate electromagnetic signals. The arrangement further includes a switching means for switchably inhibiting the drive state of the antenna. This allows in use controllable switching of the antenna in and out of the drive state to thereby control switching of signal generation on and off.

The apparatus may be otherwise referred to herein as a "sensing arrangement" since the apparatus is for use in inductive sensing.

The arrangement is particularly beneficial for use as a medical sensing arrangement, for instance for acquiring physiological measurements such as heart rate or breathing activity.

In use, the antenna, driven at resonance, generates a primary alternating electromagnetic field. When the antenna is brought into proximity with a body to be probed, the alternating field penetrates the body surface, wherein it induces circulating eddy currents within the body. These in turn induce generation of secondary magnetic fields which interact with the primary field, and alter the characteristics of the overall resultant field at the location of the loop antenna. In particular the reflected secondary fields are sensed at the antenna and effectively add an additional component of inductance to the antenna (sometimes known as a reflected inductance component). As a consequence, certain electrical characteristics of the resonator circuit (in particular the natural resonance frequency and the damping factor of the resonator circuit) undergo a slight shift.

The shift in these electrical characteristics can be sensed by signal processing components electrically coupled with the resonator circuit. By monitoring the variations in these characteristics over time, information related to movement of elements or objects within the body being probed can be derived. These can be used for example to sense certain physiological parameters or measurements such as heart rate, heart movement patterns, breathing rate or lung movement patterns during breathing. These are examples only and other physiological measurements may also be derived in other examples.

Physiological signals such as these, which exhibit an oscillatory or periodic character are sometimes known as kymographic signals.

More detail concerning the theory and application of inductive sensing using an arrangement such as that of the present invention, in particular for the purpose of sensing physiological signals, is described in document WO 2018/127482 (see for example page 14, lines 3 to page 18, line 25).

A block diagram of the basic components of an apparatus for use in inductive sensing (or a sensing arrangement) according to embodiments of the invention is shown in FIG. 1.

The apparatus or sensing arrangement 20 is for use in inductive sensing. The arrangement 20 comprises a resonator circuit 22, which in includes an inductive antenna 26, and an electrically coupled electronic signal generator 24 coupled to the antenna. The resonator circuit has a resonance frequency. The signal generator is operable to generate a, preferably oscillatory (AC), electrical drive signal to cause the antenna to generate electromagnetic signals.

The antenna is a loop antenna, and preferably is a single loop antenna, i.e. consisting of a single winding only. However, this is not essential to the invention.

The resonator circuit is configurable in a drive state in which the antenna is driven at resonance to thereby generate electromagnetic signals. Driving at resonance means for instance driving the resonator circuit such that it oscillates (electrically) at its resonance frequency. This may be achieved for instance by driving the circuit with a drive signal having a frequency matching, or substantially matching, the circuit resonance frequency.

The signal generator may be an electronic oscillator in examples, or may be any element capable of generating a drive signal for causing oscillation of the resonator circuit.

The arrangement further includes a switching means 28 which provides switchable inhibiting of said drive state. The inhibiting of the drive state is based on switchably interrupting, or adjusting electrical characteristics of, the drive signal or the resonator circuit, to thereby permit switching of electromagnetic signal generation on and off.

Multiple approaches are possible for implementing the switching of the resonator circuit drive state. In addition, and in combination with these, different particular embodiments enable control approaches for controlling multiple antennas using one or more switching means.

Various different options for implementing the switching means will first be outlined below.

According to a first set of one or more embodiments, the switching means comprises a switch element included in the resonator circuit, operable to implement a break in the circuit, at a point electrically or signally downstream from the signal generator.

The switch element can be arranged in different configurations within the resonator circuit to provide the required switchable inhibiting of the drive state.

Figure 2:
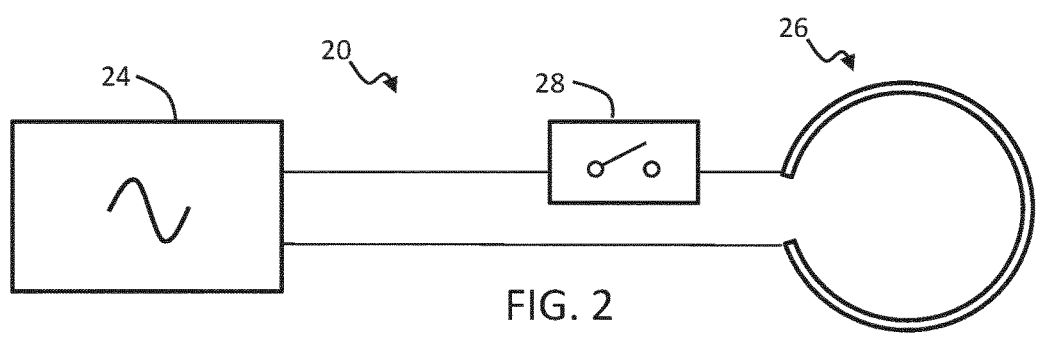
FIG. 2 shows an example sensing arrangement with a series connected switch element.

According to one set of examples, the switching means comprises a switch element connected in series with the antenna, operable to switchably decouple the antenna from the signal generator. FIG. 2 shows an example of such an arrangement.

As shown, in this example, the switching means 28 takes the form of a switch element and is included in the resonator circuit, electrically downstream from the signal generator 24, and between the signal generator 24 and the antenna 26. The switch element provides a circuit break function. It may otherwise be referred to a circuit break switch element therefore. By opening and closing the switch, a break in the circuit at the point of the component can be introduced and removed.

The switching element can be controlled to switchably decouple the antenna 26 from the signal generator, thereby interrupting the resonator circuit, and the drive signal, preventing the drive signal reaching the antenna. This stops any electromagnetic signal generation, so taking the resonator circuit out of the drive state.

By way of non-limiting example, the switch element may be implemented using a PIN diode or a (solid state) relay. Other kinds of controllable switch element (for introducing a circuit break) will be immediately apparent to the skilled person, and any may be used.

Although in the example illustrated in FIG. 2, the switch element 28 is provided electrically downstream from the signal generator 24, along a circuit track extending between the signal generator and the antenna 26, in other examples, the switch may be included internal to the signal generator. It may be provided integral to the signal generator.

By way of example, such an internal switch element may be adapted to provide adjustable or switchable supply voltage to the signal generator, or to facilitate adjustable or switchable inductance, capacitance or resistance within the signal generator internal circuitry (e.g. the oscillator circuit). Adjusting or switching of such electrical parameters may enable deactivation of the signal generator, or reduction in the output voltage of the signal generator of an amount sufficient that the resulting drive signal is not able to oscillate the antenna at resonance. Changing the capacitance, inductance or resistance of the signal generator circuitry may change the drive signal electrical characteristics sufficiently that the drive signal no longer creates a resonant oscillation in the antenna. In either case, the drive state of the resonator circuit is thereby switchably inhibited by the switching means.

Figure 3:
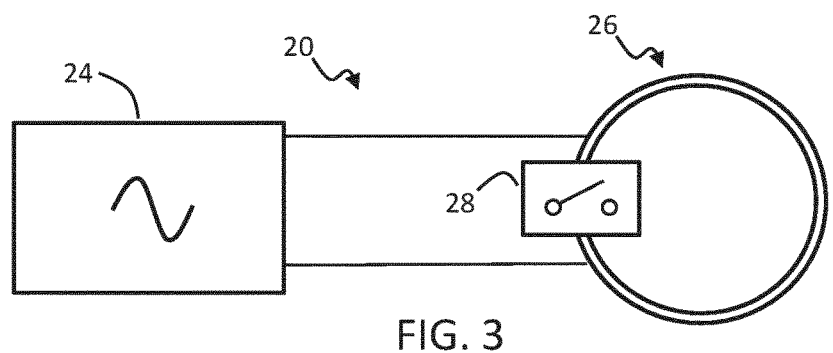
FIG. 3 shows an example sensing arrangement with a switch element connected in parallel with the antenna.

In a second set of examples, a similar switch element to that of the example of FIG. 1 may instead be provided connected in electrical parallel with the antenna 26. This example is illustrated in FIG. 3.

In this example, the switching means 28 takes the form of a switch element controllable to introduce and remove a break in the circuit by opening and closing the switch. The switch is provided along a circuit track or rail connected in parallel with the antenna 26.

When the switch 28 closes, the electrical currents will not flow through the antenna 26 but through the switch instead. The antenna is thus short-circuited. The total inductance in the resonator circuit is consequently too low for the circuit to oscillate. Thus, the drive state (in which the resonator circuit is driven at resonance) is inhibited by closing the switch. The drive state is then de-inhibited when the switch is opened.

The switch element 28 component may take the same form for example as for the series switch example of FIG. 2 above.

According to a further set of embodiments, the switching means 28 may be configured to inhibit the drive state based on altering a resonance frequency of the resonator circuit. It may provide switching or toggling of the resonance frequency between at least two values.

By changing the resonator circuit 22 resonance frequency, the resonator circuit is detuned, meaning that the drive signal generated by the signal generator 24 (of a frequency which previously brought the circuit to resonance) no longer creates a state of resonance in the resonator circuit. The switching means introduces a mismatch for instance between the frequency of the drive signal and the resonance frequency of the resonator circuit, inhibiting oscillation of the circuit at resonance. Thus, the drive state is inhibited.

The adjustment of the resonance frequency may be based on adjusting a capacitance of the resonator circuit. The resonator circuit may include a capacitor component which partially defines the resonance frequency of the resonator circuit in this example.

Figure 4:
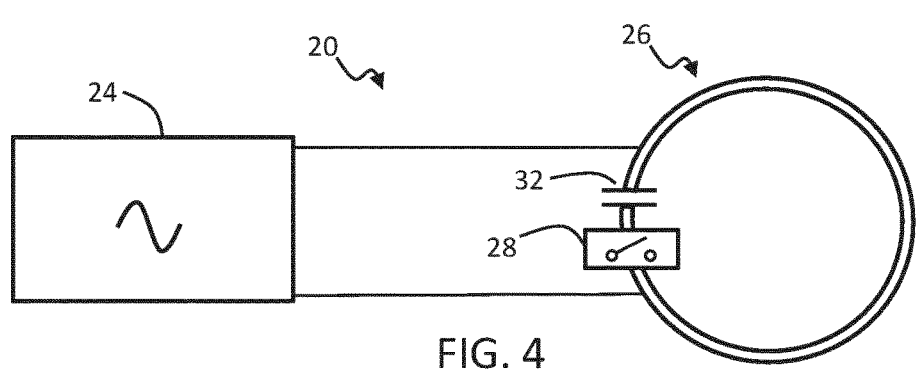
FIG. 4 shows an example sensing arrangement with an internal series switch included in the antenna loop, operable to connect and disconnect a capacitor component.

This can be implemented in different ways. FIG. 4 illustrates a sensing arrangement 20 according to one set of examples. Here, the resonator circuit 22 comprises a capacitor component 32 connected in parallel with the antenna 26, and further comprises a switching means in the forms of a switchable circuit break element 28 connected in series with the capacitor. The switchable circuit break element enables switchable decoupling of the capacitor from the resonator circuit. The capacitor is for instance provided along a sub-branch, connected in parallel with the antenna.

The switchable circuit break element 28 may take the same form as the switch element of the examples of FIGS. 2 and 3 discussed above for example.

The switching means 28 in this embodiment switchably breaks the circuit along the parallel branch or rail containing the capacitor 32. By disconnecting the parallel capacitor, the resonance frequency of the resonator circuit 22 shifts to a higher frequency. If the frequency is sufficiently high, an amplifier of the signal generator 24 will not produce sufficient amplification to start oscillation in the resonator circuit 22. Thus, a drive state, in which the resonator circuit is oscillating at resonance, is inhibited.

This set of examples provides the same benefits as the examples of FIGS. 2 and 3 above, and additionally provides a further benefit. In particular, during the inhibited (or "off" state), in addition to stopping generation of outgoing electromagnetic signals, the sensing arrangement 20 is also rendered insensitive to any incoming electromagnetic signals of the same frequency as the normal frequency of operation of the resonator circuit 22.

This is useful for example where there are other signal generation components in the vicinity which generate electromagnetic signals at the same frequency as the sensing arrangement 20, e.g. when the sensing arrangement is part of a broader sensing system, such as a magnetic resonance system. In the off state, the resonance frequency of the circuit 22 is detuned meaning the antenna and resonator circuit is also insensitive to any incoming signals of the original resonance frequency.

There may be implemented coordinated control between multiple signal sources of a broader system, and the present sensing arrangement 20, so that the resonator circuit 22 of the present sensing arrangement is off whenever other sources are on and generating electromagnetic signals.

Additionally or alternatively, in a further set of examples, the resonator circuit 22 may include a variable capacitor and include means for controlling switching of a capacitance of the capacitor between at least a first and second value, to thereby provide switchable adjustment of the resonance frequency. This thereby provides switchable detuning of the resonator circuit, and thus switchable inhibiting of the drive state.

Figure 5:
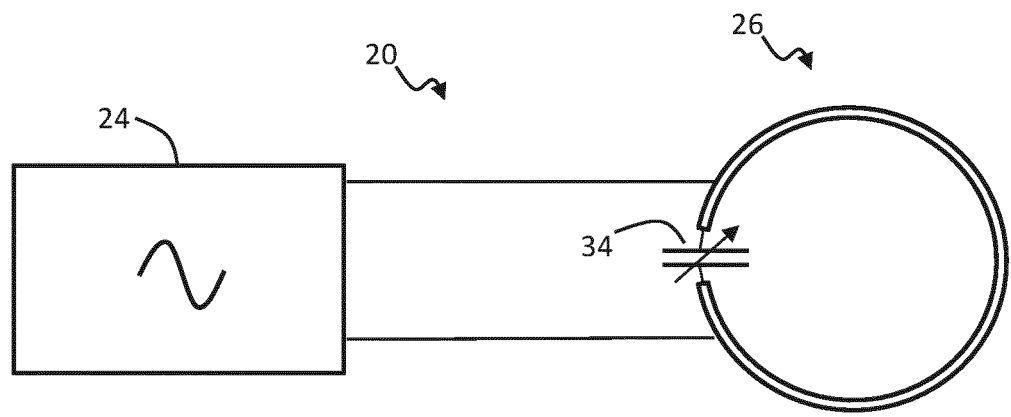
FIG. 5 shows an example sensing arrangement with a variable capacitor.

An example is shown in FIG. 5. Here, a variable capacitor 34 is provided in parallel with the antenna loop 26. However, it is possible to provide the capacitor also in series with the antenna.

By changing the capacitance, the resonance frequency of the resonator circuit 22 is altered so that there is a mismatch between circuit resonance frequency and the drive signal frequency being generated by the signal generator 24. As a consequence, the signal generator may not be able to provide enough gain to bring the resonator circuit into resonance with the drive signals it is generating. Therefore, the variable capacitor 34 can be used as a switching means for switchably inhibiting the drive state.

As noted above, a potential benefit of embodiments of the present invention is enabling avoidance of interference with signal generating components of any neighboring systems (e.g. MRI systems). This will be discussed in more detail below.

It is noted that for such purpose, the embodiment of FIG. 2 may in some cases be preferable since when the switch element 28 of this arrangement is open (putting the resonator circuit in non-active state), no current is able to flow in the loop antenna 26, regardless of the frequency of a potential external electromagnetic field received from a neighboring component or system.

In the off (shorted) state of the embodiment of FIG. 3, currents in a wide frequency range (starting from 0 Hz) may still be able to flow in the loop antenna, which may lead to some signal pickup by the arrangement and/or lead to disruption or interference of a potential neighboring system. In the off state of the embodiment of FIG. 4, there remains a (narrow, high) frequency range at which currents may be able to flow in the loop, which likewise may lead to some signal pickup and/or potential interference within a neighboring system from which such a signal has been received.

Various embodiments described above make use of a circuit break type switch element 28. In any such examples, the switch may by way of example be implemented by using a simple PIN diode. In forward bias, the PIN diode is a good radio frequency (RF) conductor and the switch in this state is 'closed' (i.e. no break in the circuit). When applying zero or a reverse bias, the PIN diode is a poor RF conductor and the switch is 'open', i.e. circuit break imposed.

Various possible switches are available in the field, which may or may not use a PIN diode internally. Any type of switch may be used.

Above have been outlined various specific implementation options for the switching means 28. However, these are not exhaustive, and it will be understood by the skilled person that other possible methods exist for inhibiting the drive mode of the resonator circuit. Any suitable approach may be used.

Other options include for instance providing an adjustable or switchable resistor in the resonator circuit, in series with the antenna, between the signal generator and the antenna. A switchable or adjustable inductance could alternatively be provided in the resonator circuit. The resistance, or inductance, could be switched between at least a first and second value to switch between drive mode and inhibition of drive mode. By changing the resistance or inductance of the circuit, the circuit is effectively detuned (i.e. the natural resonance frequency is shifted) with the result that the drive signals generated by the signal generator no longer cause resonance of the resonator circuit. This thus inhibits the drive state. In particular, changing such electrical characteristics may have the effect that the gain required to generate oscillations with the antenna, using the same drive signal, is too high for the amplifier of the signal generator to provide. Alternatively, a phase shift might be introduced as a result of the change, disturbing oscillation conditions.

In a further example, switching may comprise adjusting electrical settings of the signal generator (e.g. oscillator) to reduce the maximum achievable gain of the oscillator. As a consequence, the gain is not sufficient to create oscillation of the resonator circuit at resonance, and thus the drive state is inhibited.

In another example, the switching means may be operable to switchably disable and enable a power supply of the signal generator. This has the advantage that the power consumption is reduced to zero during the non-drive state mode. A potential disadvantage however is that this method may be slower than operating a switch arranged within the circuit. Therefore, for some potential applications, such as for capturing certain more rapid physiological or kymographic signals, this method of switching may not be fast enough to effectively capture the kymographic signals.

According to an advantageous set of embodiments, the sensing arrangement may include a controller, and wherein the controller is adapted to implement periodic switching of the switching means, to thereby impose a duty cycle on the drive signal. By duty cycling the drive signal, the time-average electromagnetic output power of the sensing arrangement during use can be reduced. Furthermore, this is reduced without necessarily reducing the maximum electromagnetic output power during the ON or HIGH phase of the duty cycle.

This enables easier compliance with electromagnetic capability (EMC) and Specific Absorption Rating (SAR) regulations, which impose a limit on the time-averaged output power of inductive sensing device.

Furthermore, this method of reducing time-averaged power output does not diminish sensing capability for the purpose of sensing oscillatory (kymographic) physiological signals such as heart rate or breathing activity. This because kymographic signals of the human body, which might be captured by the sensing arrangement in certain applications, typically exhibit slower oscillations (order of magnitude: Hz) than the typical oscillation frequency of the resonator circuit and antenna (typically in the order of magnitude: MHz). Consequently, it is not required to have a continuous measurement in order to capture the kymographic signals. It suffices to capture representative measurements, for instance by measuring the frequency and damping of the resonator circuit, only part of the time.

Figure 6:
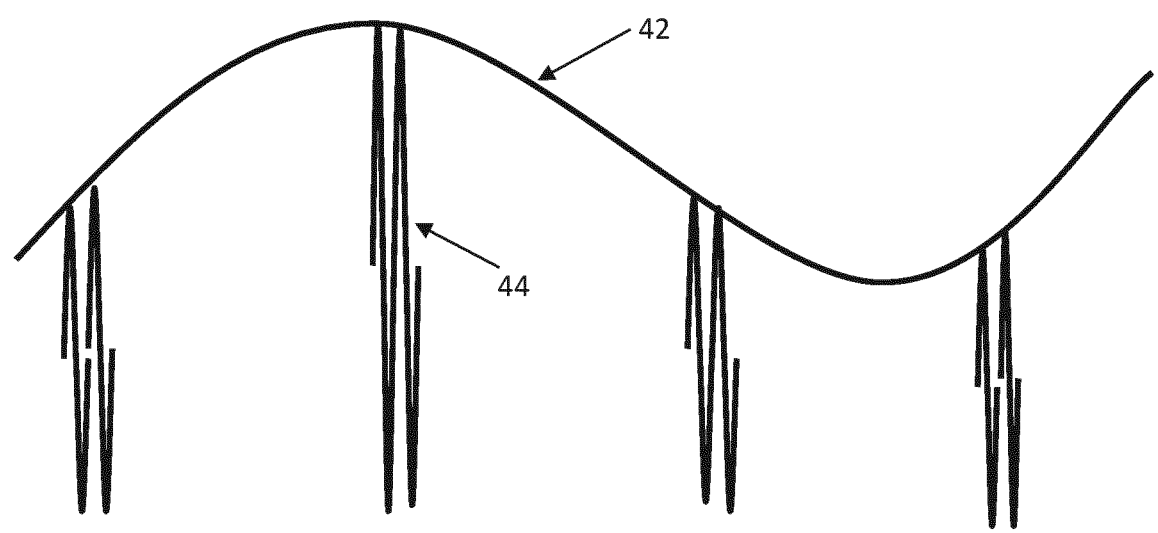
FIG. 6 illustrates use of a duty cycled sensing signal to sense an oscillatory physiological signal.

This is illustrated schematically in FIG. 6, which shows example resonator circuit oscillations 44 following an applied duty cycle, and, adjacent to this, an example physiological (kymographic) signal. It can be seen in this schematic example that the duty cycle of the generated electromagnetic (EM) signals 44 can be configured so as to follow a natural oscillation frequency of the physiological signal. In this way, the generated EM signals are still able to fully capture the physiological signal.

By thus rapidly turning on and off the drive state (i.e. duty cycling), the total radiated power over a certain timespan can be greatly reduced.

Not only does this enable easier compliance with regulations, it also reduces power consumption, thus conserving energy and potentially reducing heat generation. Sustaining oscillations consumes a constant power, which may in particular be especially high at typical frequencies of oscillation of the resonator circuit (i.e. order of MHz). The duty cycling enables reduction of average power consumption without diminishing sensing capability.

A frequency of the periodic switching (i.e. a frequency of the duty cycle) is preferably adjustable to thereby adjust an electromagnetic output power of the sensing arrangement. For example, the frequency of the periodic switching may be controllable based on a user input command, for instance receivable at a controller of the sensing arrangement via a user interface operatively coupled to the controller.

As discussed briefly above, in certain advantageous embodiments, signal generation and/or sensing may be controlled to be inhibited during an active (signal generating) state of another (proximal) signal generating component. For example, an advantageous application of embodiments of the sensing arrangement is for use within, or in conjunction with, a magnetic resonance (MR) sensing system (e.g. MM).

Roughly 3% of the time, an MM scanner emits a high power RF field, typically at 64 MHz (for a 1.5 Tesla scanner) or 128 MHz (for a 3 Tesla scanner). The loop antenna 26 of the present sensing arrangement 20 will pick up these fields if it is in an active mode, and located proximal to, or within, the Mill scanner. Not only will these external field sources interfere with signal sensing performed by the arrangement, the high power RF field may damage or even destroy the oscillator.

Therefore, in such applications, it is advisable for the resonator circuit to be switched off when the MR system RF pulse is being generated. The series switch embodiment of FIG. 2 may be the preferred embodiment as the MM RF signals will not be able to induce currents in the resonator circuit 22, since the antenna 26 is electrically decoupled from the signal generator 24, interrupting the circuit flow.

To enable this synchronized deactivation of the resonator circuit 22, according to at least one set of embodiments, there may be provided a controller for the sensing arrangement, and wherein the controller is adapted to receive in use from an external device a signal indicative of a timing of an active state of the external device, and to control the switching such that the drive state of the resonator circuit is inhibited during occurrence said active state of the external device.

For example, the controller may receive a signal indicative of timing of activation of one or more RF signal generators of an MR system, and control the switching so that the drive state is inhibited during this time. It may be switched back to non-inhibited mode after cessation of the RF loop active period.

Above have been described various options for implementing the switching means for switchably inhibiting the drive state of the sensing arrangement.

In combination with any of these options, various options exist for implementing selective switching of the drive state among a plurality of antennas provided as part of the sensing arrangement. Multiple antennas may be connected to a single signal generator, or each be provided its own signal generator, and various configurations for placement of a switch within the circuitry are also possible.

A benefit of using multiple antennas (e.g. an array of antennas) is that such a configuration can permit richer spatial information concerning the origin of a sensed physiological signal to be determined.

For example, a set of multiple antennas may be activated sequentially, in a certain spatial pattern, for example in a circulating fashion in some examples. The sequential movement from one antenna to the next may be controlled at a sufficient rate that a physiological signal, e.g. cardiorespiratory waveforms, may be sensed and resolved from each antenna. The spatial pattern of measurements enables for instance a depth of the measured signal to be more easily determined, (e.g., deep within the body, or more superficially). Alternatively, in one envisaged embodiment, an array of antennas may be embedded within a mattress. Here, information might be deduced related to a location of the patient on the mattress.

Another potential benefit of using multiple antennas is to enable a choice as to the utilized antenna for generating or sensing signals. Certain antennas in an array or arrangement may offer a stronger signal pickup. A controller of the sensing arrangement may in certain examples selectively activate a single one of the antennas which is detected as producing the strongest signal. For example, in case the multiple antennas embedded in a mattress, the loop that is closest to the thorax of the patient will typically provide the best cardiorespiratory signal.

Various example sensing arrangement embodiments will now be outlined which include a plurality of antennas.

Figure 7:
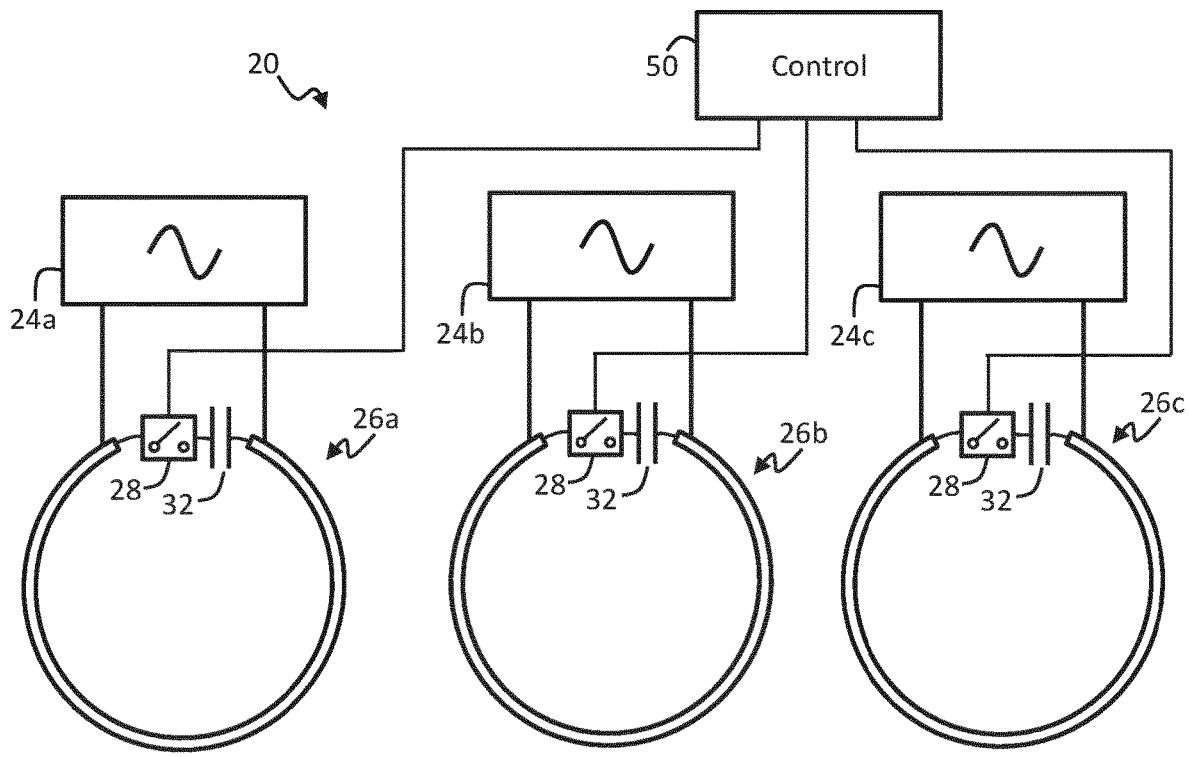
FIGS. 7 and 8 show two example sensing arrangements, each with multiple antennas, each antenna having a dedicated signal generator.
Figure 8:
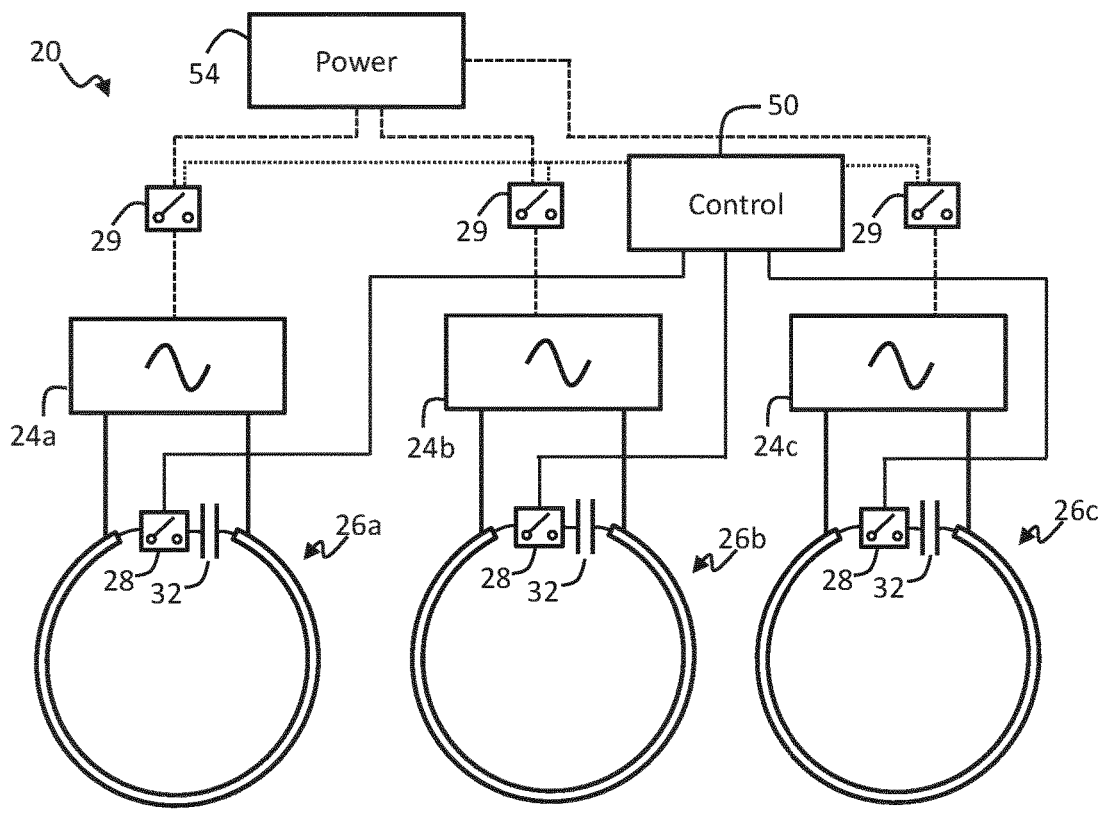

FIG. 7 and FIG. 8 illustrate a sensing arrangements 20 according to a first and second set of examples respectively. In both arrangements, a plurality of antennas 26a, 26b, 26c, is provided, each having its own dedicated signal generator 24a, 24b, 24c, e.g. oscillator. Hence, in these cases, there are effectively provided a plurality of resonance circuits, each comprising a signal generator, an antenna and a switching means.

In both example arrangements, a separate switching means is provided for each antenna in the form of a circuit break switch element 28, connected along a branch in series with the respective antenna. This switch may take the same form as discussed for the embodiments of FIG. 2, 3 or 4 above. The signal generators 24 in each example arrangement are preferably located as close as possible to the respective antenna 26 terminals to which it connects.

Each switching means 28 is connected to a controller 50 enabling central control of switching of the plural antennas/resonator circuits 22.

The series switches enable independent inhibiting or non-inhibiting of the drive state of each respective antenna. This operates for each antenna in a similar manner to the series switch mechanism of FIG. 4 above. In particular, each switch element is provided in series with the antenna and with a capacitor element, such that opening of the switch causes a shift in the resonance frequency of the local resonator circuit.

The internal series switch configuration in each of FIGS. 7 and 8 is particularly beneficial in multi-loop embodiments, since this switching method ensures that antennas switched in an "off" state have a strongly detuned resonance frequency (due to the disconnection of the capacitor element 32), thereby rendering the local resonator circuit for the antenna insensitive to the electromagnetic field produced by any other active antenna.

The arrangement of FIG. 8 is the same as that of FIG. 7 except that additional circuit break switch elements 29 are provided for each of the local resonance circuits, between a power source 54 and the signal generator 24 of each of the resonance circuits. These additional switch elements 29 enable power to be switched on and off to each respective resonator circuit. This thus provides the additional benefit of enabling power consumption to be reduced to zero for antennas 26 when they are in non-active state, by disconnecting power to the respective signal generator for the antenna.

The controller 50 may manage the complete set of switches 28, 29 in such a way that only one of the resonator circuits is active at any one time. This ensures there is no interference between signals generated and sensed at two different antennas. Preferably, for the single active resonator circuit, both of the respective switch elements 29, 28 for that circuit are set to "closed". For the remaining resonator circuits, both the power switches 29 and the loop-resonator-internal switches 28 are set to "open". This means that for the remaining non-active resonator circuits, power consumption is cut to zero, and the circuit in each is rendered insensitive to the EM-field generated by the active antenna (due to the above-mentioned detuning of the resonance frequency).

Although the switching means 28 for the examples of FIG. 7 and FIG. 8 are shown as a series switch provided internally of the antenna 26 (in series with the loop circuit line of the antenna), this represents only one possible implementation. In other examples for instance, a respective switch element may be provided connected in electrical parallel with each antenna 26. In this arrangement, the switching means for each respective antenna would take a similar form to the example switching means of FIG. 3 described above. In this example, closing the switch causes short-circuiting of the respective antenna 26, meaning that the antenna no longer oscillates and no longer generates electromagnetic signals.

The internal series switch arrangement illustrated in FIG. 7 and FIG. 8 may however be preferable in certain cases to a parallel switch arrangement due to the fact that, in the parallel switch embodiment, the antenna 26 is not truly de-coupled from the rest of the resonator circuit, meaning there remains the potential for electromagnetic signals from neighboring antenna to be sensed by the deactivated antenna. However, in most practical implementations, this would not be expected to occur due to the fact that the self-resonance frequency of the short-circuited antenna loop is typically much higher than that of the broader resonator circuit (and hence the likely operating frequency of neighboring antenna). As a result, incoming EM signals would be unlikely to lead to resonant pickup at the short- circuited antenna.

FIGS. 9-12 show various example embodiments for antenna arrangements 20, each comprising multiple antennas 26, and each comprising only a single signal generator 24 for driving the set of antennas. The different embodiments show different possible implementations of switching means 28 for implementing selective switching of inhibiting or non-inhibiting of the drive state in each antenna.

An advantage of using a single signal generator 24 for multiple antennas 26, rather than a separate signal generator for each antenna, is reduced cost due to fewer required components. General manufacturing complexity is also reduced, as well as potentially the power consumption.

The circuit path between the signal generator 24 and each antenna 26 is preferably as short as possible, as the connecting wire path contributes inductance to the circuit. Hence, a long wire path will contribute a large inductance, which may prove problematic for certain high frequencies of operation, as high frequency drive signals do not in general travel well along long wire tracks. However, providing a short wire track between each antenna and a central signal generator may be challenging for some applications, in particular in cases where a spatial arrangement for the antennas is desired which has the different antennas fairly widely spaced from one another. An example may be an arrangement in which the antennas are provided embedded at different places within a mattress.

Hence, for such cases, an arrangement having a separate signal generator for each antenna (as in the examples of FIGS. 7 and 8 may be preferable).

The various examples of FIGS. 9-12 will now be described.

Figure 9:
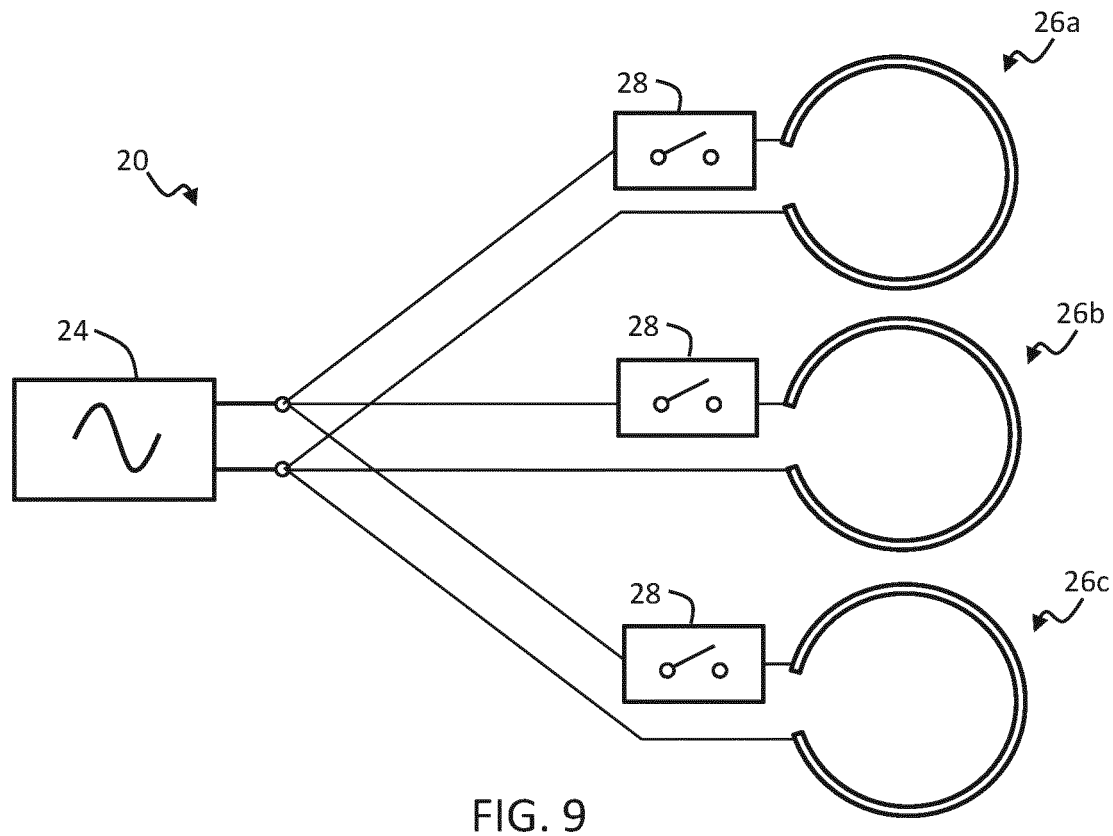
FIGS. 9-12 show various example sensing arrangements comprising multiple antennas, and wherein a single signal generator is provided for the whole set of antennas.

In the example of FIG. 9, a single signal generator 24 (e.g. an oscillator) is electrically coupled to each of three antennas 26a, 26b, 26c. A separate respective switch element 28 is provided connected in series between the signal generator and each respective antenna 26. The switch is operable to introduce a break in the circuit path to the respective antenna 26 when 'opened' while leaving circuit paths to the other antennas unaffected.

Figure 10:
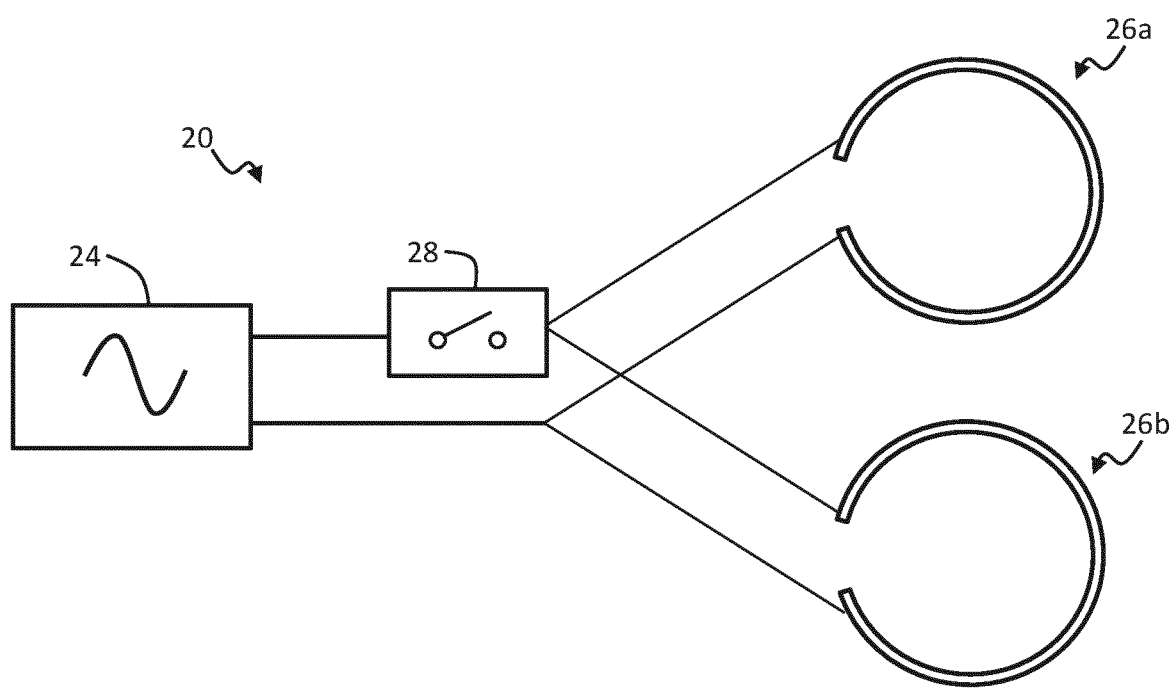

In FIG. 10, the example sensing arrangement 20 is shown comprising two antennas and a single signal generator. Here, the switching means comprises an N-port switch 28 provided in series along one outgoing rail of the signal generator 24. One end of the switch is connected to this outgoing terminal. The other end of the switch is alternately connectable to a first terminal of the first antenna 26a and a first terminal of the second antenna 26b. As second terminal of each antenna is connected to the second outgoing terminal of the signal generator 24.

A greater number of antennas 26 may be provided in other arrangements, with the N-port switch being alternately connectable at said other end to each of them.

The N-port switch has the effect that the drive signal generated by the signal generator 24 can only ever be provided to a single antenna 26 at once, resulting in exclusive selective activation of antennas.

Figure 11:
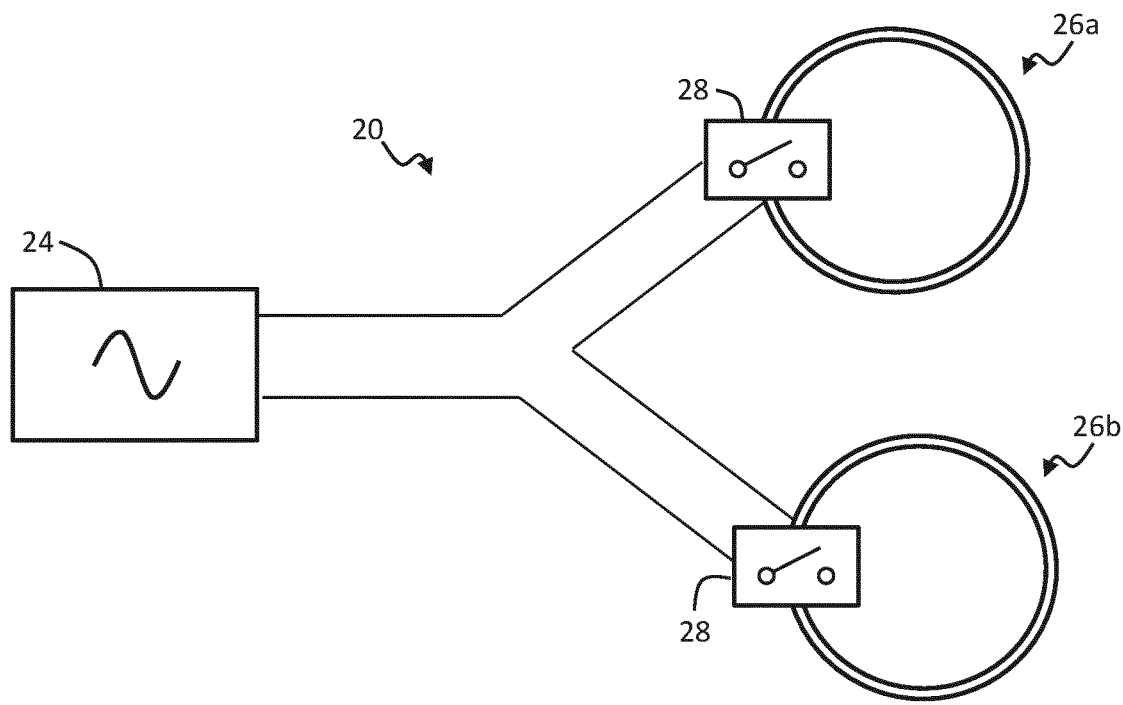

FIG. 11 shows a further example sensing arrangement comprising multiple antennas 26 connected to a single signal generator 24. Switching means is provided in this example in the form of a separate switch element 28 connected in parallel with each of the antennas. The switch element for each antenna is provided in the same configuration as the parallel switch in the example arrangement 20 of FIG. 3 described above.

The switch element 28 can be opened or closed to connect or disconnect a branch running parallel to the respective antenna 26. By closing the switch, the antenna is short-circuited, meaning that current will not flow through the respective antenna, and so electromagnetic signal generation is inhibited in the respective antenna.

A controller may be provided (not shown) arranged for controlling the two switch elements 28 to thereby facilitate central control of switching of the multiple antennas.

Figure 12:
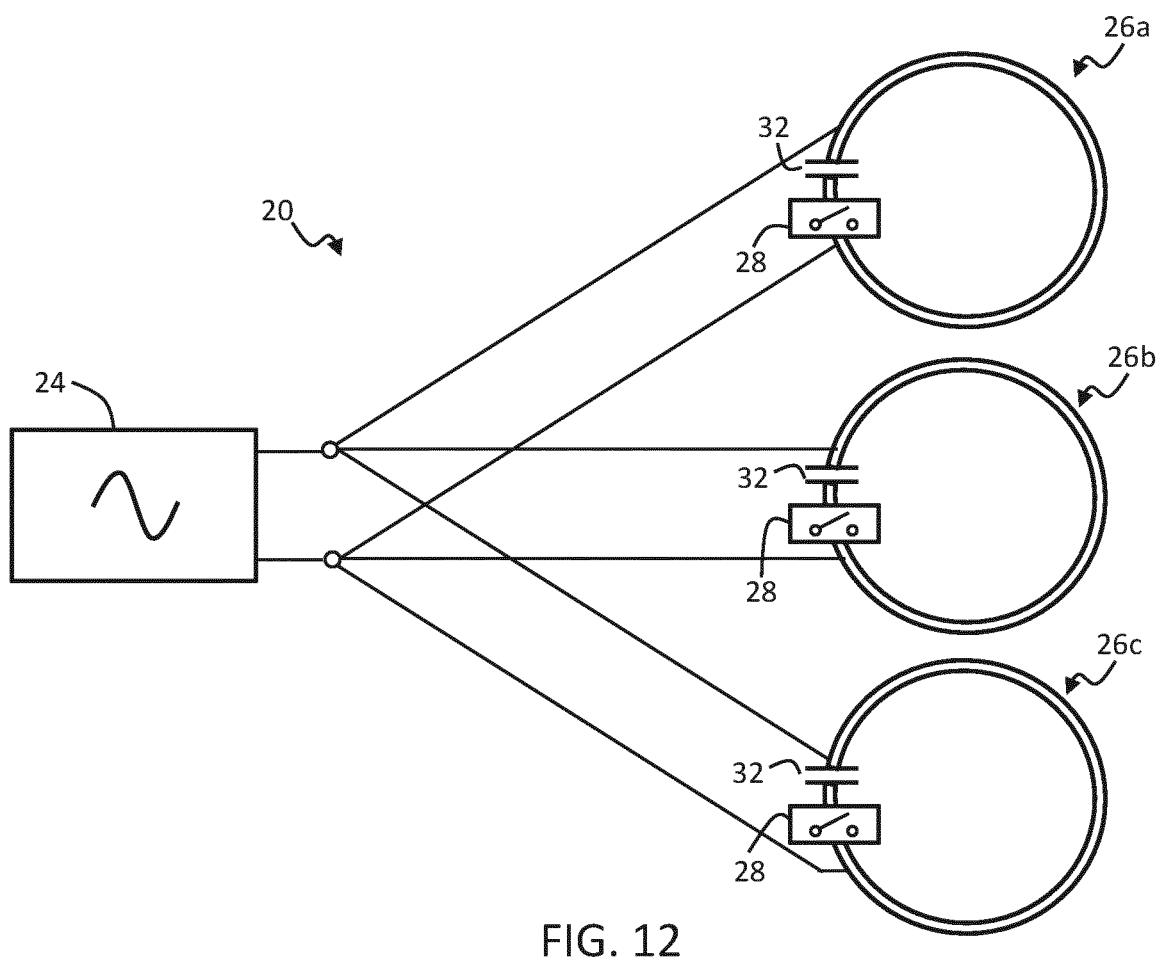

FIG. 12 shows a further example sensing arrangement 20 comprising multiple antennas 26a, 26b, 26c. In this example, the switching means is provided in the form of a separate internal series switch element 28 connected in series with each antenna, via a respective tuning capacitor 32. The switch for each respective antenna in this arrangement has the same configuration as the switch in the example of FIG. 4 (and FIGS. 7 and 8). When each respective switch element 28 is opened, the capacitor 32 is disconnected from the respective antenna 26, causing a shift in the resonance frequency at the respective antenna, meaning that oscillation at resonance no longer occurs (assuming the drive signal is maintained at the same frequency, i.e. substantially matching the original resonance frequency of the resonator circuit before detuning). Accordingly, electromagnetic signal generation is inhibited.

Although in the various multi-antenna embodiments described above, and shown in FIGS. 7-12, a specific number of antennas is shown in the arrangement, this is not limiting, and any number of antennas can in general be provided.

A further aspect of the invention may provide an inductive sensing system, comprising
a sensing arrangement in accordance with any example or embodiment outlined above or described below, or in accordance with any claim of this application; and
a signal processing unit for receiving and processing electromagnetic signals sensed at the antenna of the arrangement to derive one or more sensing measurements.

The sensing measurements are preferably physiological signals, e.g. kymographic physiological signals such as heart movement or heart rate signals or breathing or respiration signals.

As discussed above, when the primary magnetic field generated by the antenna penetrates a body to be sensed, eddy currents are induced in the body which in turn generate secondary 'reflected' magnetic fields which are sensed at the antenna. These effectively lead to addition of a secondary inductance component (reflected inductance) to the resonator circuit, which leads to changes in (or detuning of) certain electrical characteristics of the resonator circuit, in particular the natural resonance frequency and the damping factor. By measuring this detuning of the electrical characteristics, information related to movement of objects inside the probed body can be deduced.

Hence, according to embodiments of the above aspect of the invention, a sensing system is provided having signal processing components in electrical communication with the resonator circuit configured to sense variations over time of electrical characteristics of the resonator circuit. From these, the signal processing unit, or a different operatively coupled component, may determine one or more sensing measurements. These may in advantageous embodiments be physiological parameters or signals, e.g. kymographic signals as mentioned above.

The signal processing unit may include a pre-stored algorithm, or have pre-stored programming, for deriving from the detected variations in said electrical characteristics, measurements of one or more physiological parameters.

More detail on options for implementing processing of the resonator circuit electrical characteristics to derive physiological parameter measurements is provided in document WO 2018/127482. Suitable signal processing apparatus is described for example between page 27, line 32 and page 31, line 29.

In preferred embodiments, the antenna 26 is provided having a single loop (single winding), though this is not essential. A single loop winding provides benefits in terms of signal strength since parasitic capacitive coupling between windings is reduced. The same single loop antenna is used to both generate the excitation signals and to sense the returned signals. The returned signals may be sensed simultaneously with signal generation by detecting changes in the electrical characteristics of the resonator circuit while the signals are being generated (and returned signals are being received at the antenna). A combined sensing and generating antenna allows for provision of high-quality sensing signals as well as providing benefits of low-cost, low complexity, and low-power.

As discussed above, certain embodiments may make use of a controller. A controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Examples in accordance with a further aspect of the invention provide a method of configuring a sensing arrangement, the sensing arrangement comprising
a resonator circuit comprising an antenna, and an electronic signal generator coupled to the antenna, for driving the antenna with a drive signal to cause it to generate electromagnetic signals, the resonator circuit having a resonance frequency,
wherein the resonator circuit is configurable in a drive state in which the antenna is driven at resonance to thereby generate electromagnetic signals, and
the method comprising: controlling switchable inhibiting of said drive state, the inhibiting based on interruption or alteration the drive signal or of the resonator circuit, to thereby control start or stop of electromagnetic signals.

Implementation options and details for each of the above steps may be understood and interpreted in accordance with the explanations and descriptions provided above for the apparatus aspect of the present invention (i.e. the sensing arrangement aspect).

Any of the examples, options or embodiment features or details described above in respect of the apparatus aspect of this invention (in respect of the sensing arrangement) may be applied or combined or incorporated mutatis mutandis into the present method aspect of the invention.

A wide range of potential applications for embodiments of the invention exist. By way of non-limiting example, applications include: patient monitoring; telemetry; spot-check monitoring; implementation in wearable devices (e.g. chest patches or wrist worn devices); neonatal monitoring; sleep monitoring; obstetrical monitoring; use for mattress-based sensors.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. An apparatus for use in inductive sensing for application to a body to be investigated, the apparatus comprising:
    a resonator circuit including a loop antenna and an electronic signal generator coupled to the antenna,
        wherein the electronic signal generator is configured to emit a drive signal to drive the loop antenna,
        wherein driving the loop antenna causes the loop antenna to generate electromagnetic signals,
        wherein the resonator circuit has a resonance frequency, and
        wherein the resonator circuit is configurable in a drive state in which the loop antenna is driven at resonance to generate electromagnetic signals for application to the body; and
    a switch connected in electrical parallel with the antenna, wherein the switch is configured to inhibit the drive state to permit switching of electromagnetic signal generation by at least one of interrupting and adjusting the electrical characteristics of at least one of the drive signal and the resonator circuit.

2. The apparatus as claimed in claim 1, further comprising a controller configured to control the switch.

3. The apparatus as claimed in claim 2, wherein the controller is configured to control the switch in accordance with at least one of a defined control schedule and a control program.

4. The apparatus as claimed in claim 2, wherein the controller is configured to
    communicate with an external device;
    receive from the external device a signal indicative of a timing of an active state of the external device; and
    control the switch such that the drive state of the resonator circuit is inhibited during an occurrence of the active state of the external device.

5. The apparatus as claimed in claim 2,
    wherein the controller is adapted to implement periodic switching of the switch; and
    wherein the periodic switching imposes a duty cycle on the drive signal.

6. The apparatus as claimed in claim 5,
    wherein a frequency of the periodic switching is adjustable;
    wherein adjusting the frequency of the periodic switching adjusts a time-average electromagnetic output power of the apparatus; and
    wherein the frequency of the periodic switching is controllable based on a user input command received at the controller via a user interface operatively coupled to the controller.

7. The apparatus as claimed in claim 1,
    wherein the switch includes a controllable switch element connected in series between the signal generator and the antenna; and
    wherein the controllable switch element is configured to permit switchable decoupling of the antenna from the signal generator.

8. The apparatus as claimed in claim 1, wherein the switch includes a switch element connected in electrical parallel with the antenna for switchably short-circuiting the antenna.

9. The apparatus as claimed in claim 1, wherein the switch is configured to inhibit said drive state based on altering the resonance frequency of the resonator circuit.

10. The apparatus as claimed in claim 9, wherein the switch includes at least one of
    a capacitor connected in parallel with the antenna, and a switch element in series with the capacitor for switchably decoupling the capacitor from the resonator circuit, and
    a variable capacitor connected in parallel with the antenna, wherein the variable capacitor includes a variable capacitor controller for controlling switching of a capacitance of the variable capacitor between a first value and a second value to adjust the resonance frequency.

11. The apparatus as claimed in claim 1,
    wherein the resonator circuit includes a second loop antenna operatively coupled to the signal generator;
    wherein the signal generator is configured to supply a first drive signal to the loop antenna and a second drive signal to the second loop antenna; and
    wherein the switch is configured to permit selective inhibiting of the drive state in at least one of the loop antenna and the second loop antenna.

12. The apparatus as claimed in claim 1, further comprising,
    a second resonator circuit including a second loop antenna;
    a second switch for the second resonator circuit, and
    a controller for controlling the switch and the second switch.

13. The apparatus as claimed in claim 11 wherein switch is configured to supply one drive signal at a time.

14. An inductive sensing system for application to a body to be investigated, the inductive sensing system comprising:
    a resonator circuit, including a loop antenna and an electronic signal generator coupled to the antenna,
        wherein the electronic signal generator is configured to emit a drive signal to drive the loop antenna,
        wherein driving the loop antenna causes the loop antenna to generate electromagnetic signals,
        wherein the resonator circuit has a resonance frequency, and
        wherein the resonator circuit is configurable in a drive state in which the loop antenna is driven at resonance to generate electromagnetic signals for application to the body;
    a switch connected in electrical parallel with antenna, wherein the switch is configured to inhibit the drive state to permit switching of electromagnetic signal generation by at least one of interrupting and adjusting the electrical characteristics of at least one of the drive signal and the resonator circuit; and a signal processor configured to:
- receive one or more electromagnetic signals sensed at the loop antenna, and
- derive one or more measurements associated with the one or more electromagnetic signals.

15. An inductive sensing system for application to a body to be investigated, the inductive sensing system comprising:
- a resonator circuit including a loop antenna and an electronic signal generator coupled to the antenna,
- wherein the electronic signal generator is configured to emit a drive signal to drive the loop antenna,
- wherein driving the loop antenna causes the loop antenna to generate electromagnetic signals,
- wherein the resonator circuit has a resonance frequency, and
- wherein the resonator circuit is configurable in a drive state in which the loop antenna is driven at resonance to generate electromagnetic signals for application to the body;
- a switch connected in electrical parallel with the antenna, wherein the switch is configured to inhibit the drive state to permit switching of electromagnetic signal generation by at least one of interrupting and adjusting the electrical characteristics of at least one of the drive signal and the resonator circuit; and
- a signal processor configured to:
  - detect, using the loop antenna, one or more electromagnetic signals returned from the body responsive to the one or more electromagnetic signals, wherein the detection of the one or more electromagnetic signals is based on detecting a variation of electrical characteristics of the resonator circuit over time, and
  - derive one or more sensing measurements.

16. The inductive sensing system of claim 15, wherein an electromagnetic signal detection by the signal processor and an electromagnetic signal generation by the loop antenna overlap.

* * * * *